United States Patent

Harsh et al.

[11] Patent Number: 5,205,833
[45] Date of Patent: Apr. 27, 1993

[54] DEVICE FOR REMOVING HYPODERMIC NEEDLES FROM SYRINGE BARRELS

[76] Inventors: Don J. Harsh, 5670 S. 920 East;
Linda R. Hills, 6298 S. Lorreen Dr., both of Salt Lake City, Utah 84121;
Kennalyn Howard, 3706 Market St., West Valley City, Utah 84119

[21] Appl. No.: 747,395

[22] Filed: Aug. 16, 1991

Related U.S. Application Data

[63] Continuation of Ser. No. 465,910, Jan. 16, 1990, abandoned, Continuation-in-part of Ser. No. 158,767, Feb. 28, 1988, Pat. No. 4,904,244.

[51] Int. Cl.$^5$ .......................... A61M 5/00; A61M 5/31
[52] U.S. Cl. .................................. 604/240; 604/243; 604/263
[58] Field of Search ............... 604/192, 198, 241, 242, 604/240, 263, 187, 110, 243; 128/919

[56] References Cited

U.S. PATENT DOCUMENTS

| | | | |
|---|---|---|---|
| 3,491,757 | 1/1970 | Arce | 128/221 |
| 4,139,009 | 2/1979 | Alvarez | 128/218 N |
| 4,237,882 | 12/1980 | Wickham | 128/218 N |
| 4,425,120 | 1/1984 | Sampson et al. | 604/198 |
| 4,490,142 | 12/1984 | Silvern | 604/241 |
| 4,568,336 | 2/1986 | Cooper | 604/240 |
| 4,592,744 | 6/1986 | Jagger et al. | 604/192 |
| 4,596,562 | 6/1986 | Vernon | 604/192 |
| 4,631,057 | 12/1986 | Mitchell | 604/198 |
| 4,655,751 | 4/1987 | Harbaugh | 604/198 |
| 4,664,653 | 5/1987 | Sagstetter et al. | 604/197 |
| 4,681,567 | 7/1987 | Masters et al. | 604/198 |
| 4,693,708 | 9/1987 | Wanderer et al. | 604/198 |
| 4,747,835 | 5/1988 | Sandhaus | 604/192 |
| 4,752,291 | 6/1988 | Magrath | 604/240 |
| 4,890,619 | 6/1989 | Hughes | 604/187 |
| 4,898,588 | 2/1990 | Roberts | 604/187 |
| 4,904,244 | 2/1990 | Harsh et al. | 604/187 |
| 4,927,019 | 5/1990 | Haber et al. | 206/356 |
| 4,973,317 | 11/1990 | Bobrove | 604/198 |

FOREIGN PATENT DOCUMENTS 883053  7/1949  Fed. Rep. of Germany .

OTHER PUBLICATIONS

"It Happened Here!".
"University of Utah, Occupational Health Memorandum" dated Jan. 11, 1988.

*Primary Examiner*—C. Fred Rosenbaum
*Assistant Examiner*—Mark O. Polutta
*Attorney, Agent, or Firm*—Madson & Metcalf

[57] ABSTRACT

A generally cylindrical structure of rigid material is configured such that the device is capable of at least partially circumscribing at least a portion of a syringe barrel. Near one end of the cylindrical structure, the apparatus is provided with a structure for secure attachment to the base of a hypodermic needle.

The structure for secure attachment to the base of a hypodermic needle may vary depending on the specific structure of the apparatus and the type of needle used. In one embodiment of the device, the means of attachment comprises "Luer" threads on the interior surface of the cylindrical structure. Those threads, in turn, engage the base of a typical needle and the device provides twisting engagement with the needle base.

Using the device removal of the needle from the syringe barrel is simple and safe. The structure is simply pressed in a forward direction (i.e., away from the syringe barrel in the direction of the needle) until the needle becomes disengaged form the needle socket of the syringe barrel. Thus, the needle is removed without the necessity of encountering the needle point. In that the pushing action is relatively gentle, the needle detaches relatively slowly and has very little tendency to become a dangerous projectile.

17 Claims, 1 Drawing Sheet

DEVICE FOR REMOVING HYPODERMIC NEEDLES FROM SYRINGE BARRELS

This application is a continuation of U.S. patent application Ser. No. 07/465,910, filed Jan. 16, 1990, now abandoned, and entitled "Device For Removing Hypodermic Needles From Syringe Barrels," which is a continuation-in-part of patent application Ser. No. 07/158,767, filed Feb. 28, 1988, now U.S. Pat. No. 4,904,244, and entitled "Apparatus For Safely Removing Needles From Hypodermic Syringes".

BACKGROUND OF THE INVENTION

1. Field of the Invention

The present invention is related to an apparatus for accomplishing the safe removal of used needles from hypodermic syringes. More particularly, the present invention relates to an apparatus for pushing needles off a syringe without the necessity of grasping or recapping the used needle.

2. Background of the Invention

A very serious practical problem in medical treatment is the removal of needles from hypodermic syringes once those needles have been used. Often syringes and needles are disposed of separately. As a result, it is necessary, after each injection or other use of a hypodermic syringe, for the medical personnel to attempt to remove the needle from the syringe for disposal. The removal of a needle from a syringe, however, is a potentially dangerous procedure.

Installing a new needle on the end of a syringe in preparation for use is generally quite safe and easy in that needles are packaged in solid plastic sheaths, or in some other similar manner that covers the needle point until the needle is securely installed on the syringe. Thus, the plastic sheath or the like can be safely grasped and the needle can be securely fit onto the end of the syringe, either by friction or by twisting the needle onto a "Luer" connection. The sheath is designed for easy removal once the needle is secured to the syringe body. Thus, installation of the needle takes place without exposing the user to the needle point.

Removal of used needles from the ends of syringes is a much more difficult and potentially dangerous process. Initially, it must be recognized that the needle is not capped at the time of removal. Some users inevitably attempt to recap the needles before removal. This procedure is not the generally preferred method of disposal and can result in accidental penetration of the needle into the hands and arms of the medical personnel in the event that the user is unable to immediately fit the cap over the needle. Such needle penetrations are often referred to as "needle sticks."

Thus, medical personnel are faced with the problem of undoing a friction attachment, or with twisting and pulling a needle, in order to eject it from the end of the syringe body. This obviously presents a substantial danger of injury due to penetration by the exposed needle point.

In many hospitals and other medical facilities, needle sticks are far and away the most frequent cause of injury to medical personnel. For example, in one major university hospital it was found that there were 199 reported incidents of "needle stick" in a single year, and it was not unusual to find 20-30 reported needle stick accidents in any particular month.

In a survey of the causes of needle sticks, it was found that the greatest instances of such accidents occurred during disposal of the needles, or in attempting to recap the needle following use. Thus, as would be expected, penetration by used needles, rather than by fresh needles, is the major source of injury.

The potential for serious and painful injury following penetration by used hypodermic needles is obvious. Uncontrolled penetration of an individual by any extremely sharp object can result in serious physical injury. Indeed, needle sticks can cause injury similar to penetration by a small knife or other sharp instrument.

Apart from the potential for serious physical injury, an additional serious problem with needle sticks is the transmission of disease. In that needles are often used to give injections to seriously ill individuals, it is not surprising to find the transmission of communicable diseases by way of needle stick. This has become a particularly serious problem in recent years due to the spread of acquired immune deficiency syndrome (AIDS) and other diseases transmitted by exposure to blood or body fluids.

Medical and hospital personnel are taking ever increasing precautions to minimize the transmission of diseases such as AIDS in the hospital setting. These precautions include increased use of masks, gloves, and even goggles when treating individuals with certain ailments. It will be readily appreciated that a single needle stick can quickly defeat all of the precautions taken in other areas.

While AIDS is of major concern, other communicable and infectious diseases can also easily be transmitted by way of needle stick. Any type of infectious disease could be passed along to the medical personnel by penetration with a used needle. Diseases ranging from hepatitis to the common cold are of concern.

While various attempts have been made to address the problem of penetration by used needles, no widely accepted solution has been developed. For example, devices which basically include the use of an outer sheath on the syringe barrel have been developed. When the needle is not in use, the sheath slides forward until it covers the tip of the exposed needle. Many different configurations of this type of device are known in the art.

It will be appreciated, however, that constructing a needle sheath does not deal directly with the problem of removal of used needles from syringe bodies. Sheaths of the type mentioned above simply allow medical personnel to cover the needle while it is still attached to the hypodermic syringe Thus, these types of sheaths do not in actuality deal with the problem of needle removal. These devices simply help protect the needle point between uses.

Other types of sheaths have also been developed. For example, collapsible sheaths which are permanently mounted to the exterior of the needle have been developed. When the needle is used during injection, the sheath collapses or folds toward the syringe barrel. When the injection is completed, the sheath again expands covering the needle. These mechanisms, however, simply provide means for covering an exposed needle while the needle is not in use.

While some of the sheaths described above may be fit with a feature which aids in the removal of the needle, this type of device is not very useful in everyday practice. The sheaths are cumbersome, expensive, and are not easily retrofit onto conventional, commonly used syringes. As a result, these devices do not solve the problem of needle removal in common practice. Needle sheaths of the type described are more adaptable for use in situations requiring specialized equipment and repeated use of the needle.

In order to solve the problem of needle removal in everyday practice it is necessary to develop a device which allows needles to be removed from conventional, widely used syringe types. In addition, since cost and convenience are both important considerations, it would be desirable to provide an inexpensive and disposable mechanism for removing such needles. Such a mechanism would necessarily be compatible with inexpensive, disposable syringes and needles. A mechanism which requires reuse and sterilization is cumbersome and labor intensive and, as a result, is not practical for everyday use.

Accordingly, it would be a significant advancement in the art to provide an apparatus which aided medical personnel in removing used needles from hypodermic syringes. It would be a further advancement in the art if such a device could be used in connection with conventional and widely accepted syringe types. In particular, it would be an advancement in the art if such a device could be retrofit onto conventional existing syringes. It would also be an advancement in the art to provide a simple and inexpensive device for removal of used needles from syringe bodies. This would allow the device to be disposed of along with the used syringe and needle once use was completed.

Such methods and apparatus are disclosed and claimed herein.

BRIEF SUMMARY AND OBJECTS OF THE INVENTION

The present invention is related to an apparatus for use in removing used needles from the ends of hypodermic syringes. As discussed above, the removal of used needles from syringes is a difficult and often dangerous procedure. The present invention overcomes the problems of the prior art and provides a simple, inexpensive, and easily used device for removing such used needles.

The basic concept of the present invention is to push or twist needles off the end of a syringe barrel without causing the needle to become a projectile. The removal procedure is accomplished entirely without exposing the user of the needle to the sharp needle point. Thus, the person using the syringe is much less likely to be injured by penetration of the needle and by the resulting transmission of disease.

In one preferred embodiment, the device comprises a generally cylindrical structure of rigid material. The cylindrical structure is configured such that the device is capable of at least partially circumscribing at least a portion of a syringe barrel. Near one end of the cylindrical structure, the apparatus is provided with means for secure attachment to the base of a hypodermic needle.

The means of secure attachment to the base of a hypodermic needle may vary depending on the specific structure of the apparatus and the type of needle used. In one embodiment of the device, the means of attachment comprises "Luer" threads on the interior surface of the cylindrical structure. Those threads, in turn, engage the base of a typical needle and the device provides twisting engagement with the needle base.

Using the device, removal of the needle from the syringe barrel is simple and safe. The structure is simply pressed in a forward direction (i.e., away from the syringe barrel in the direction of the needle) until the needle becomes disengaged from the needle socket of the syringe barrel. Thus, the needle is removed without the necessity of encountering the needle point. In that the pushing action is relatively gentle, the needle detaches relatively slowly and has very little tendency to become a dangerous projectile.

The device may take a variety of configurations. For example, the cylindrical structure may be composed of two separate sections. The first section is larger in diameter in order to enable the device to fit over a syringe barrel. The second section of the cylindrical structure may be somewhat smaller in diameter in order to more easily engage the base of the needle. Incorporated within the interior of the second section are the threads, or other means, for engaging the needle.

Alternatively, the structure may have a uniform outside shape (such as a cylindrical shape). The interior of the structure, however, is shaped in order to fit over the syringe barrel at one end and to engage the needle at the other end.

In a third embodiment, the engaging means is modified. The engaging means may snap over the needle base in order to provide secure engagement. The remainder of the device may be constructed in the same manner as are the other embodiments.

Accordingly, it is a principal object of the present invention to provide an apparatus for safely removing used needles from the ends of hypodermic syringes.

It is a related object of the present invention to provide an apparatus which will allow medical personnel to remove needles from syringes without the necessity of grasping the needle or performing any manual function in the vicinity of the needle point.

It is also an object of the present invention to provide means for moving the needle in a forward direction such that the needle base becomes disengaged from the needle socket of the syringe barrel.

It is an additional object of the present invention to provide such an apparatus which allows for easy retrofit onto conventional syringes and which is simple and economical to manufacture and use.

These and other objects of the present invention will become apparent upon reading the following detailed description and appended claims and upon reference to the accompanying drawings.

DETAILED DESCRIPTION OF THE PREFERRED EMBODIMENTS

Figure 1:
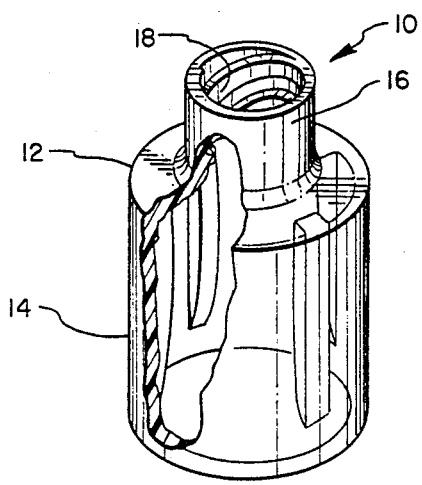
FIG. 1 is a partially cut away cross sectional view of one embodiment of the present invention.

The present invention can be more fully understood with reference to the drawings, wherein like parts are designated with like numerals throughout. Referring more particularly to FIG. 1, a first embodiment of the apparatus of the present invention is illustrated. The present invention is related to an apparatus for aiding in the removal of needles from the ends of hypodermic syringes without the necessity of touching the needle.

FIG. 1 illustrates one embodiment of the present invention, generally designated 10. The embodiment of the device as illustrated in FIG. 1 comprises a generally cylindrical body 12 which is composed of two generally cylindrical sections. The rear or base section 14 is configured generally such that it is capable of circumscribing at least a portion of the barrel of a conventional syringe. As will be discussed in greater detail below, when the device is in operation, base section 14 covers the forward portion of the syringe barrel, as well as at least part of the needle socket of the syringe barrel.

The other cylindrical section of the cylindrical body is the forward section 16. Forward section 16 is also generally cylindrical and is securely attached or molded to the front opening of the base or rear section 14. Forward section 16 includes means for securely, but removably, attaching the device 10 to the base of a needle. In the embodiment of the invention illustrated in FIG. 1, the attachment means comprises threads 18 of the type used in Luer Lock devices. As will be more fully appreciated with reference to the discussion of FIGS. 3 through 5, the threads are configured such that they are capable of engaging the base of a conventional hypodermic needle.

Figure 2:
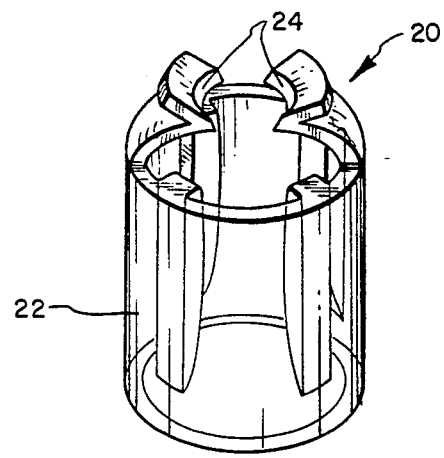
FIG. 2 is a partially cut away cross sectional view of another embodiment of the present invention.

An alternative embodiment of the device is illustrated in FIG. 2. As illustrated in FIG. 2 the invention is generally designated 20. Device 20 is also generally cylindrical in shape, but consists of a single cylindrical section 22. The device 22 also includes means for attachment to the base of a syringe. The attachment means comprises teeth 24 which snap over the lip on the base of a conventional needle. The teeth 24 provide two functions. First they secure the needle base to the syringe barrel during the injection. Second, they grip the needle base sufficiently that the needle base can be disengaged from the syringe barrel when cylindrical section 22 is slid forward. The interior of the cylindrical section 22 is shaped such that it is capable of fitting over the necessary components of the needle and syringe while the exterior diameter of the device is uniform.

Figure 3:
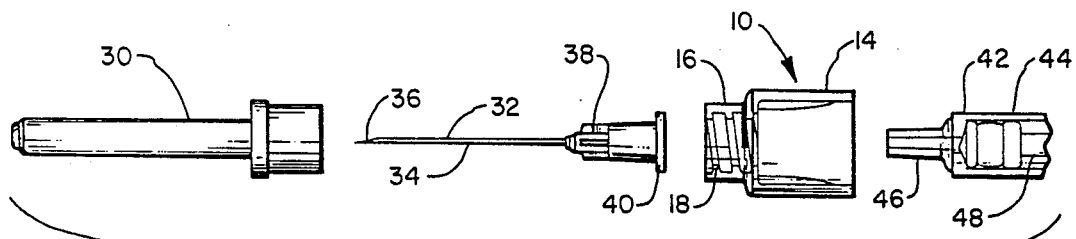
FIG. 3 is an exploded perspective view of one embodiment of the present invention, as well as a needle sheath, a hypodermic needle, and a hypodermic syringe.

The manner in which the present invention is used in connection with a syringe is illustrated in FIG. 3. In FIG. 3, the device as shown in FIG. 1 is illustrated. FIG. 3 is an exploded view of the device and the various conventional components of a syringe. Proceeding from right to left, the first component illustrated is a needle cap or sheath 30. Typically, needles are sold with a needle cap or sheath, of the type illustrated, already in place. This allows the person working with the syringe and needle the ability to safely install the needle on the syringe. Thus, needle sticks during installation are avoided.

The next component is a conventional hypodermic needle 32. The needle is comprised of a shaft 34 having a needle point 36. Attached to the rear of the shaft 34 is a needle base 38. The base is constructed such that it is easily attached to the needle socket of a conventional hypodermic syringe. One of the features of many conventional needles 32 is a lip 40. Lip 40 extends outwardly around the circumference of the base 38 and can be used as a point of attachment of the needle to the device 10. In particular, threaded engagement can be achieved by twisting lip 40 into threads 18.

The next component of the combined structures is the device 10 of the present invention. The structure and function of the device 10 is discussed further herein. However, the device is configured generally such that it engages the needle at one end, but slides over the exterior of the syringe barrel at the opposite end.

The next illustrated component is a conventional hypodermic syringe 42. The hypodermic syringe is comprised of a syringe barrel 44. The forward end of the syringe barrel 44 is enclosed by means of a needle socket 46. The needle socket 46 is specifically configured such that it is capable of receiving and securely attaching a conventional needle base, such as base 48. Thus, a secure but detachable friction engagement is achieved between the needle 32 and the syringe barrel 44. Reciprocating within the interior of the syringe barrel 44 is a plunger 48. Plunger 48 is constructed such that when it is withdrawn, liquid can be drawn into the syringe barrel 44. When the plunger is pushed forward, the liquid contents of the syringe are forced out of the syringe barrel 44 through the needle 32.

Figure 4:
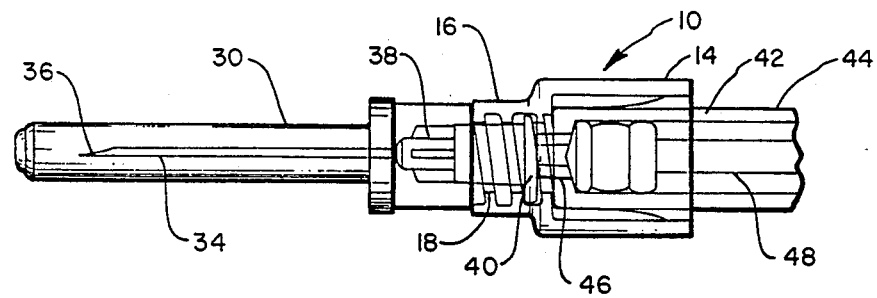
FIG. 4 is a cross-sectional view of one embodiment of the present invention in place on a hypodermic syringe.

The components described in FIG. 3 are shown as assembled in FIG. 4, but with the sheath 30 removed from the needle. As can be appreciated with reference to FIG. 4, the needle 32 is placed over the needle socket 46 and a friction fit is achieved. The present invention can also be used with needles and sockets which are threaded and result in a threaded engagement.

FIG. 4 also illustrates the manner in which the present invention is used. The device 10 is placed over the forward portion of the syringe barrel 44. The length of the syringe barrel 44 covered by the device 10 is variable and within the discretion of the user, and may vary depending on the particular context in which the device 10 is used.

The threads 18 engage the lip 40 of the needle 32. The threads are appropriately configured such that a threaded engagement can be achieved by simply twisting the lip of the needle base through the threads 18 on the device 10. Other means of engagement between the device and the needle 32 are certainly possible and are to considered to be within the scope of the present invention. For example, the needle base 38 can be configured such that it includes threads which correspond to the threads 18 on the device 10.

Alternatively, the device 10 can be configured such that the lip of the base of the needle snaps into the device 10 as shown in FIG. 2. Teeth 24 are placed such that the lip 40 of the needle 22 snaps between teeth 24. Thus, the needle is securely attached to the syringe barrel by both friction engagement and the teeth 24. At the same time, the teeth aid in removal of the needle in the manner described below.

When the needle has been used it is a simple manner to disengage the needle from the syringe for proper disposal. The user simply slides the device 10 or 20 forward over the syringe barrel 44 until the needle 32 becomes disengaged from the needle socket 46. This can be done in an easy and controlled movement such that the needle does not become a dangerous flying object, but rather drops into a needle box or other similar disposal container.

Figure 5:
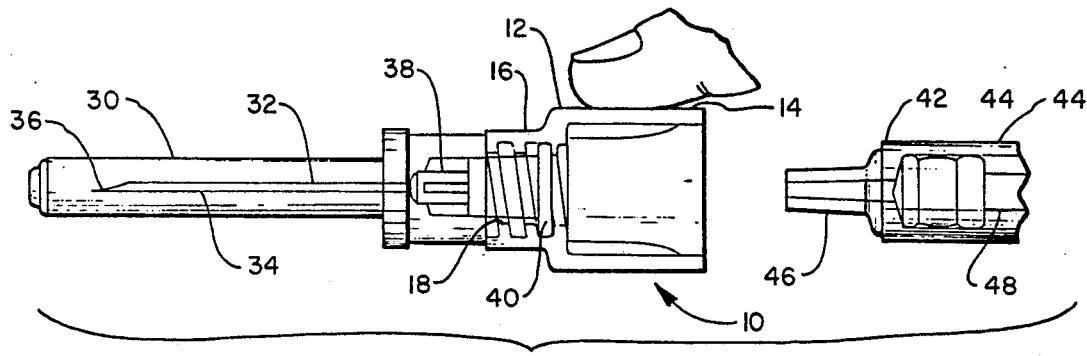
FIG. 5 is a cross-sectional view of the device as shown in FIG. 4 in the process of removing a needle from the needle socket of the hypodermic syringe.

This operation is generally illustrated in FIG. 5. In FIG. 5 the device 10, still attached to the needle 32, is shown being moved off the end of the syringe barrel 44. It will be appreciated that this removal operation takes place without the necessity of grasping the needle, attempting to replace the sheath 30, or otherwise encountering the point 36 of the needle 32. When the base of the needle 38 disengages from the needle socket 46, the needle and the device can be easily discarded. Accordingly, accidental needle sticks are avoided.

It will be appreciated that the present invention can be formed of a variety of materials. For example, a medical grade plastic material may be preferable. Thus, it would be an easy matter to form a disposable device which is compatible with conventional and widely accepted disposable syringes. Alternatively, the device may be formed of metal, graphite, or other desirable material. It is only necessary that the material be sufficiently durable and flexible to perform the desired function and sufficiently inexpensive that it can be economically disposed of along with the needle.

In summary, the present invention accomplishes all of the objects set forth above. The present invention provides methods and apparatus for safely removing used needles from the ends of hypodermic syringes. The removal of needles is a major cause of personal injury and accidents among hospital and medical personnel. Thus, the present invention provides a major safety feature at a reasonable cost. Furthermore, the present invention in its several embodiments can be retrofit onto conventional and readily available syringes.

The present invention allows medical personnel to remove needles without the necessity of grasping the needle or attempting to recap the syringe. It is simply necessary to grasp the syringe barrel and, with one finger, move the device forward a sufficient distance to force the needle to disengage the needle socket. Thus, all direct contact with the used needle is avoided. Thus, it will be appreciated that a major improvement in the art has been accomplished through the present invention.

It will be appreciated that the apparatus and methods of the present invention are capable of being incorporated in the form of a variety of embodiments, only a few of which have been illustrated and described above. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for removing needles from hypodermic syringes without re-capping said needles, said syringes comprising a barrel and a needle socket attached to one end of the barrel, the needle socket configured such that a needle can be removably attached to said needle socket, the apparatus comprising:
a structure capable of being slidably mounted over the exterior of at least a portion of a syringe barrel and over at least a portion of a needle socket, the structure having means for attachment to said needle such that said needle, while attached to said structure, is capable of being securely attached to the needle socket, said apparatus further comprising an opening configured such that the needle can be placed directly onto the needle socket of the syringe while said apparatus is positioned over the syringe barrel and needle socket, and when the needle is securely attached to the needle socket the attachment of the needle to the needle socket secures the apparatus to the syringe, such that if the apparatus is slid forward with respect to the syringe barrel, the apparatus causes the needle to disengage from the needle socket.

2. An apparatus for removing needles from hypodermic syringes as defined in claim 1 wherein said means of attachment to said needle is capable of securing the apparatus to the needle after the needle has been removed from the syringe barrel.

3. An apparatus for removing needles from hypodermic syringes as defined in claim 1 wherein said means for attachment to said needle comprise threads.

4. An apparatus for removing needles from hypodermic syringes as defined in claim 1 wherein said threads are configured such that they are capable of securely engaging a needle base.

5. An apparatus for removing needles from hypodermic syringes as defined in claim 1 wherein the exterior of said apparatus is generally cylindrical, such that the apparatus is capable of surrounding at least a portion of said syringe barrel.

6. An apparatus for removing needles from hypodermic syringes as defined in claim 1 wherein said means of attachment to said needle comprises teeth.

7. An apparatus for removing needles from hypodermic syringes as defined in claim 6 wherein said teeth are configured such that they are capable of snappingly engaging a needle base.

8. An apparatus for use in removing needles from hypodermic syringes without re-capping said needles, said hypodermic syringes comprising a syringe barrel and a needle socket, the apparatus comprising a structure having means for secure attachment to the base of a needle, the apparatus being configured such that it is capable of being slidably mounted over at least a portion of a syringe barrel and at least a portion of a needle socket, said apparatus further configured such that a needle can be mounted onto the apparatus while the apparatus is mounted over said syringe barrel and said needle socket, but such that the needle is capable of being directly attached to the needle socket of the syringe barrel, such that if said structure is slid forward with respect to the syringe barrel, the structure causes the needle to disengage from the needle socket.

9. An apparatus for use in removing needles from hypodermic syringes as defined in claim 8 wherein said means of attachment to the base of a needle comprises threads disposed on at least one end of said apparatus.

10. An apparatus for use in removing needles from hypodermic syringes as defined in claim 9 wherein said means of attachment comprises at least one tooth disposed on said apparatus such that it is capable of engaging a needle base.

11. An apparatus for use in removing needles from hypodermic syringes as defined in claim 8 wherein said cylindrical structure comprises two attached cylindrical sections.

12. An apparatus for use in removing needles from hypodermic syringes as defined in claim 8 wherein said apparatus is constructed of medical grade plastic.

13. A device for effecting removal of hypodermic needles from a hypodermic syringe, said hypodermic syringe having a syringe barrel and a needle socket, said device comprising:
a first generally cylindrical portion capable of circumscribing at least a portion of a syringe barrel;

a second generally cylindrical portion capable of circumscribing at least a portion of a needle socket, said second portion further comprising threads disposed within the interior of said second portion and capable of engagement with the base of a hypodermic needle;

means for securely joining said first and second cylindrical portions; and means for securing a hypodermic needle to said second portion such that the needle, while secured to the device, is capable of being attached directly to a needle socket when the device is positioned on the syringe and such that the attachment between the needle and the needle socket provides means for securing the device to the syringe.

14. A device for effecting removal of hypodermic needles from a hypodermic syringe as defined in claim 13 wherein said first portion is configured such that it is slidable over at least a portion of a syringe barrel.

15. A device for effecting removal of hypodermic needles form a hypodermic syringe as defined in claim 14 wherein the device is configured such when the device is secured to a needle, and the needle is attached to a needle socket, sliding the device forward with respect to a syringe barrel results in disengagement of the needle from the needle socket.

16. A device for effecting the removal of hypodermic needles from a hypodermic syringe as defined in claim 13 wherein the device is configured such that when a needle is secured to the device and the needle is placed on a needle socket, the attachment of the needle to the needle socket secures the device to the syringe.

17. A device for effecting removal of hypodermic needles from a hypodermic syringe, said hypodermic syringe having a syringe barrel and a needle socket, said device comprising:

a first generally cylindrical portion capable of circumscribing at least a portion of a syringe barrel;

a second generally cylindrical portion capable of circumscribing at least a portion of a needle socket wherein said second portion further comprises means for snappingly engaging the base of a hypodermic needle;

means for securely joining said first and second cylindrical portions; and means for securing a hypodermic needle to said second portion such that the needle, while secured to the device, is capable of being attached directly to a needle socket when the device is positioned on the syringe and such that the attachment between the needle and the needle socket provides means for securing the device to the syringe.

* * * * *